US009125688B2

(12) United States Patent
Fowler

(10) Patent No.: US 9,125,688 B2
(45) Date of Patent: Sep. 8, 2015

(54) INSEMINATION APPARATUS AND METHOD

(71) Applicant: Jana Fowler, Vallejo, CA (US)

(72) Inventor: Jana Fowler, Vallejo, CA (US)

( * ) Notice: Subject to any disclaimer, the term of this patent is extended or adjusted under 35 U.S.C. 154(b) by 201 days.

(21) Appl. No.: 13/862,699

(22) Filed: Apr. 15, 2013

(65) Prior Publication Data
US 2014/0309488 A1    Oct. 16, 2014

Related U.S. Application Data

(60) Provisional application No. 61/687,104, filed on Apr. 18, 2012.

(51) Int. Cl.
*A61B 17/43* (2006.01)
(52) U.S. Cl.
CPC ...................... *A61B 17/43* (2013.01)
(58) Field of Classification Search
CPC ..... A61H 19/00; A61H 19/02; A61H 19/027; A61H 19/44; A61H 2201/105; A61H 2201/1253
USPC .......................................... 600/38–41, 33–35
See application file for complete search history.

(56) References Cited

U.S. PATENT DOCUMENTS

| | | | | |
|---|---|---|---|---|
| 5,405,326 | A * | 4/1995 | Haber et al. | 604/110 |
| 7,163,508 | B1 * | 1/2007 | Washington | 600/38 |
| 7,189,200 | B2 | 3/2007 | Chen | |
| 2009/0163765 | A1* | 6/2009 | Chen | 600/35 |
| 2009/0171144 | A1* | 7/2009 | Squicciarini | 600/38 |
| 2011/0224482 | A1 | 9/2011 | McCarthy et al. | |
| 2012/0143001 | A1* | 6/2012 | Case | 600/38 |
| 2012/0184921 | A1* | 7/2012 | Brillant | 604/239 |
| 2013/0324792 | A1* | 12/2013 | Mizrahi et al. | 600/38 |

* cited by examiner

*Primary Examiner* — Samuel Gilbert
(74) *Attorney, Agent, or Firm* — Howard Cohen

(57) ABSTRACT

An apparatus and method for in vivo fertilization through self-insemination includes sleeve fabricated of soft silicone elastomer having a tubular portion and a distal bulbous head. The sleeve may be secured concentrically about a syringe approximating the size, configuration, and feel of a human penis. The bulbous head includes lobes arrayed at equal angles about the head, adjacent lobes being separated by narrow channels extending longitudinally to provide a flow space for air and fluids. The distal stem of the syringe extends through the sleeve at the distal end thereof. Thus seminal fluid discharged from the syringe will be ejected out of the central opening in the head of the sleeve.

10 Claims, 2 Drawing Sheets

INSEMINATION APPARATUS AND METHOD

CROSS-REFERENCE TO RELATED APPLICATIONS

This application claims the benefit of the filing date priority of Provisional Application No. 61/687,104, filed Apr. 18, 2012.

FEDERALLY SPONSORED RESEARCH

Not applicable.

SEQUENCE LISTING, ETC ON CD

Not applicable.

BACKGROUND OF THE INVENTION

1. Field of the Invention

This invention relates to insemination devices for human use and, more particularly, to insemination devices that may be used for self-insemination in a non-medical setting.

2. Description of Related Art

There has been a notable increase in interest in and use of in vivo fertilization as a preferred method of procreation. Some factors that may be responsible for this are the newfound ability and acceptance of single women to have children, and the stability and domesticity afforded by the recent public approval of same-sex marriage.

Although in vivo fertilization is a medical term and implies a medical procedure, there is really no necessity for it to be relegated to a doctor's office, clinic, or medical center. The basic biological factors remain unchanged: a viable sperm cell must be delivered to an egg cell so that they may combine to form a zygote, a fetus, and ultimately a live newborn. Any woman may obtain seminal fluid from a male, such as from a sperm bank, or a donation from a friend, colleague, or stranger. In the past, the seminal fluid was placed in a syringe-like device (commonly, the "turkey baster technology"), inserted into the vagina, and discharged in the hope that it would find its way to the cervix and eventually to the ovum within the uterus.

The prior art devices that are commercially available are not designed for self-insemination, and are not user-friendly in that regard. For example, a vial of seminal fluid from a sperm bank may cost $400-$600 for 1 cc, and given that high cost it is desirable to use it in a way that maximizes its potential for fertilization success. The hit-or-miss syringes available commercially do nothing to maximize the potential.

BRIEF SUMMARY OF THE INVENTION

The present invention generally comprises an apparatus and method for in vivo fertilization through self-insemination, without requiring medical personnel and the attendant expense. It does not require any previous experience or medical training or professional license to use, and it is user-friendly. Furthermore, the invention delivers the seminal fluid directly to the cervix to optimize the fertilization process, and mimics the comfort and feeling of a natural process. That is, the invention is intended to aid in inducing an orgasm, during which the cervix widens and actively participates in the body helping to "collect" the sperm through the uterus and fallopian tubes. This function is beyond the scope of medical procedures performed by doctors, and is more easily carried out in the privacy and comfort of the user's home, using this invention. The method of the invention achieves the same likelihood of successful conception as in a medical office using medical instruments.

The apparatus of the invention includes a syringe of standard design and having a length and diameter that approximates those same dimensions of a human penis. The distal end of the syringe tapers to a narrow diameter stem having a distal opening extending axially therethrough. A sleeve fabricated of soft silicone elastomer is provided, including a tubular portion and a distal bulbous head. The inner diameter of the sleeve is approximately the same as the outside diameter of the syringe, so that the sleeve may be secured concentrically about the syringe. The assembled sleeve and syringe approximate the size, configuration, and feel of a human penis, with the syringe providing the rigidity for inserting the assembly into the vagina. The bulbous head includes three lobes arrayed at equal angles about the axis of the assembly, the adjacent lobes being separated by narrow channels extending longitudinally in the head from the distal tip to the tubular portion. The channels provide a flow space for air and fluids, so that the assembled apparatus does not force air inwardly when it is inserted in the vagina, nor does it create a vacuum during withdrawal of the device that might otherwise create suction that dislodges the seminal fluid from the region adjacent to the cervical opening.

An axially extending passageway extends through the sleeve at the distal end thereof, and is dimensioned to accept the distal stem of the syringe, with the discharge opening of the stem being directly adjacent to the distal end of the passageway in the sleeve. Thus seminal fluid discharged from the syringe will be ejected out of the central opening in the head of the sleeve. A shallow recess is formed in the distal end surface of the head, and provides spacing between the distal tip of the syringe and the distal end of the sleeve. This prevents the syringe tip from jutting out of the sleeve and poking into surrounding sensitive tissue.

The method of the invention includes an optional step of providing a cannula that is configured to be frictionally placed about the stem of the syringe, with a length suitable to extend into and access the contents of a vial or specimen cup of seminal fluid. Fluid is drawn through the cannula into the syringe by withdrawing the plunger, and the cannula is removed and the neck is capped to retain the fluid. A sliding bail, comprised of a flat panel having a central opening that slidably receives the barrel of the syringe, and two opposed tab handles that extend radially beyond the tabs extending from the proximal end of the barrel, is joined to the proximal end of the syringe. The sleeve is then installed about the distal end of the syringe and slidably worked into place until the capped tip extends through the passageway in the head of the sleeve. The cap is removed and the loaded inseminator is introduced into the vagina.

It may be appreciated that the inseminator approximates the size and feel of a typical penis, and may be used by a woman in the traditional way to aid in having an orgasm. At the appropriate moment, ideally when the distal tip is proximate the cervical os, the plunger may be depressed to discharge the seminal fluid. It is believed that discharging the seminal fluid in the midst of or just following an orgasm increases the potential for fertilization to be successful.

After the device is used, the sliding bail may be employed by slidably working it along the barrel in the distal direction to peel the proximal end of the sleeve from the barrel of the syringe. The sleeve may be removed and cleaned in boiling water or compatible antiseptic techniques, and the syringe may be disposed and replaced for subsequent use.

DETAILED DESCRIPTION OF THE INVENTION

Figure 1:
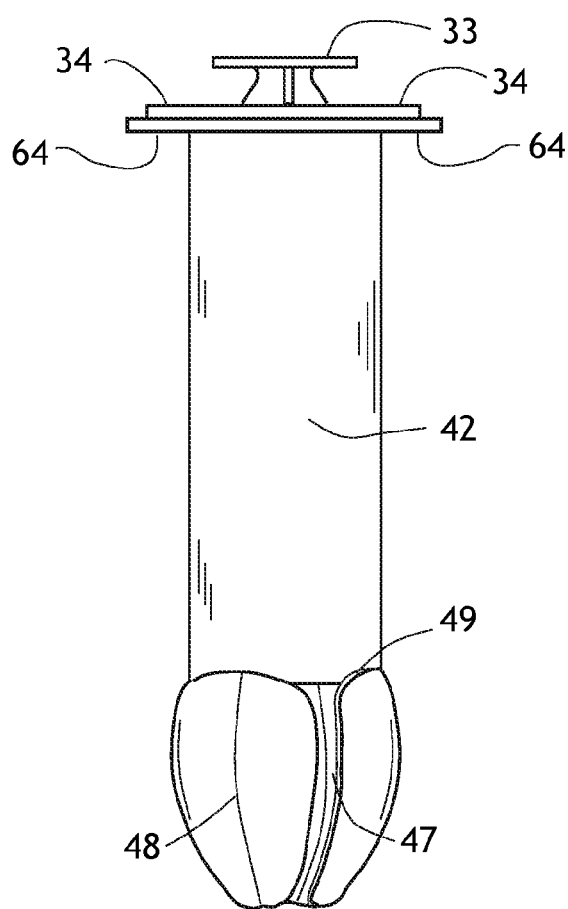
FIG. 1 is a plan view of the inseminator assembly of the present invention.

The present invention generally comprises an apparatus and method for in vivo fertilization through self-insemination, without necessitating medical personnel and the attendant expense. Furthermore, the invention delivers the seminal fluid directly to the cervix to optimize the fertilization process, and mimics the comfort and feeling of a natural process.

With regard to FIGS. 2 and 6, one component of the apparatus is a syringe 21 which is similar in construction to prior art devices, with the exceptions noted below. The syringe includes a tubular cylindrical barrel 22 having a proximal open end 23 and a closed distal end that tapers to a narrow diameter stem 24 extending axially and having a distal opening 26. A plunger 27 extends axially and slidably in the bore 28 of the barrel 22. The plunger has a distal tip 29 formed of a resilient elastomer, and longitudinally extending ribs 32 extending proximally parallel to the axis of the barrel. The tip 29 has a distal conical surface 31 with a blunt vertex. The surface 31 is complementary to the interior tapering surface of the bore 28, so that there is no residual space in the barrel 28 when the plunger is extended fully distally, and no fluid is retained and lost in the barrel. At the proximal end of the plunger a push pad 33 extends transverse to the axis of the device and provides a surface for the user to engage with a thumb or palm to push the plunger distally, and also serves as a grip for pulling and translating the plunger proximally in the bore 28. A pair of tabs 34 extends in diametrical opposition at the proximal end of the barrel 21 to facilitate grasping the barrel and translating it in opposition to the plunger.

Figure 2:
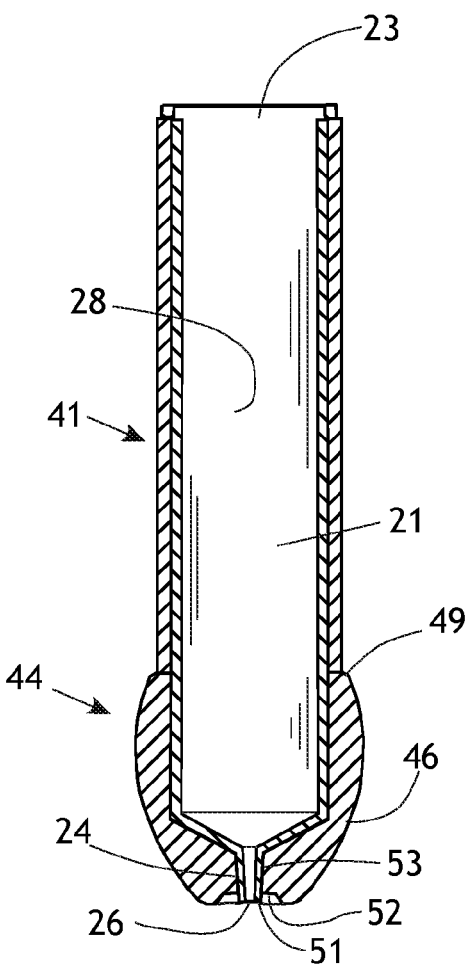
FIG. 2 is a cross sectional longitudinal view of the assembled sleeve and syringe barrel of the invention.
Figure 3:
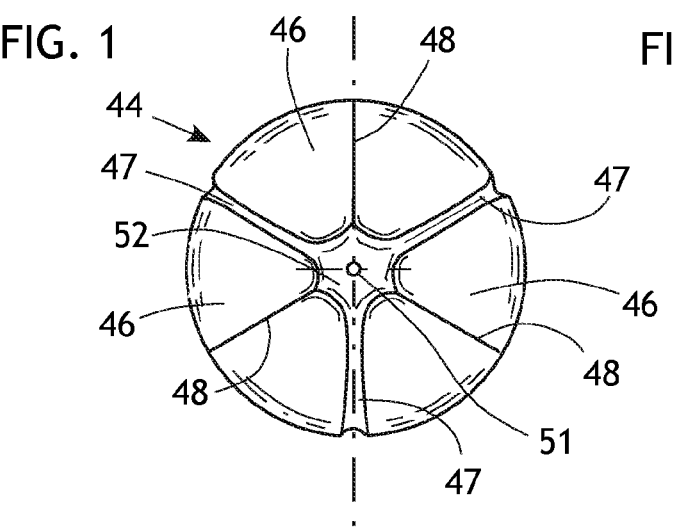
FIG. 3 is an end elevation of the distal head of the inseminator assembly shown in FIGS. 1 and 2.
Figure 4:
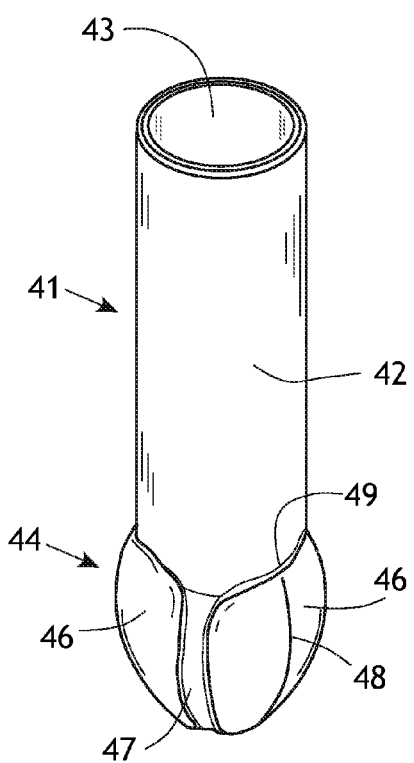
FIG. 4 is a perspective view of the inseminator assembly shown in FIGS. 1-3.

With regard to FIGS. 1, 2, and 4, another key component of the inseminator is a sleeve 41 that is configured to be secured about the syringe 21. The sleeve 41 is fabricated of silicone elastomer, and includes a tubular portion 42 having a proximal opening 43 and a bulbous closed distal head portion 44. The inner diameter of the sleeve 41 is approximately the same as the outside diameter of the syringe barrel 21, so that the sleeve 41 may be secured concentrically about the syringe with an elastic, frictional engagement that prevents relative longitudinal translation therebetween.

The head end 44 includes a trio of lobes 46 that each describe an oblate shape that extends slightly radially from the tubular portion 42 at their junctions 49 and curve smoothly radially inwardly and distally as well as curve about the longitudinal axis of the assembly. The lobes 46 are arrayed at equally spaced angles about the axis, and each lobe 46 is separated from its adjacent lobes by one of a trio of channels 47 that extend longitudinally parallel to the axis. The lobes 46 stand in relief from the tubular portion 42, whereas the channels 47 extend in negative relief in the surface of the head end 44. The thickness of the lobes, combined with the softness of the elastomer from which the sleeve is fabricated, creates a soft cushion that encompasses the distal end of the syringe barrel 22.

In addition, a trio of groove lines 48 extend longitudinally, each bisecting a respective one of the lobes 46. At the center of the distal end 44 a narrow, axially aligned passageway 53 extends from the interior of the sleeve 41 to a discharge opening 51. The passageway 53 is dimensioned to receive the stem 24 of the syringe with the distal opening 26 of the stem being directly adjacent to the discharge opening 51 at the end of the passageway in the sleeve. Thus seminal fluid discharged from the syringe 21 will be ejected out of the discharge opening 51 in the head 44 of the sleeve 41. A shallow recess 52 is formed in the distal central surface of the end 44. It provides spacing between the distal tip of the syringe and the distal-most end of the sleeve to prevent the syringe tip from jutting out of the sleeve and poking into surrounding sensitive tissue.

The channels 47 and grooves 48 provide a flow space for air and fluids, so that the assembled apparatus does not force air inwardly when it is inserted in the vagina, nor does it create a vacuum during withdrawal of the device that might otherwise create suction that dislodges the seminal fluid from the region adjacent to the cervical opening.

The distal tip 29 of the plunger 27 of the syringe is slightly larger in diameter than a typical medical syringe plunger, creating quite a bit of frictional resistance in the plunger when it is depressed. This helps to prevent poor injections or accidental injections, and the increased compression of the tip against the sides of the syringe forms an extremely tight seal. Because the plunger has such an effective seal, when the contents of the syringe are ejected, none of the fluid will be remain behind on the inner walls. This is extremely important, particularly since seminal fluid is very expensive, and each drop counts and can be the difference between an successful or failed attempt to achieve fertilization.

The overall syringe capacity is chosen for the perfect amount of pressure of liquids exiting the syringe when the plunger is engaged. In a preferred embodiment the volumetric capacity of the syringe is approximately 60 cc, with a length of about 5 inches (127 mm) and a width of about 1⅛ inches (28.5 mm).

The syringe 21 is capable of effectively simulating the natural flow of fluids from an average male human to enhance the user's experience both sensually and also mechanically. While typically insemination is carried out by medical personnel using a standard 3 inch syringe, the syringe of this invention has a strong force of injection behind it to help disperse the materials within into the correct and most effect areas during insemination. Moreover, the syringe is relied upon not only to take up, store, and eject the seminal fluid, it also provides the structural size, length, girth, and stiffness to support the sleeve to mimic an erect penis. The sleeve in turn provides the softness, elasticity, and "touch" that emulates natural flesh.

The sleeve is made of silicone elastomer, the industry standard for other devices to be inserted in a vagina (recreational sex toys). Silicone is used because of its realistic skin-like feel, easiness to clean, natural inertness to chemical reactions, and deterrence to harboring biological organisms. It is also the best material for this purpose because, while its manufacturing is complex, difficult, and expensive, it is the highest quality material:

1) It is hypoallergenic and inert, thereby eliminating most adverse reactions.
2) It is latex free, and made from completely inorganic materials, with no rubber/latex product or hybrid product constituents.
3) Silicone is flexible and easy to manipulate or stretch.
4) It is phthalate free, and made from high quality platinum silicone materials.
5) Coloring is FDA approved food grade standards.
6) The silicone compound is chosen to be easy to sterilize
7) Silicone elastomer has sufficient tensile strength to prevent micro rips or ripples in the fabric of the sleeve that would potentially hold any bacteria or retain any microorganisms after use and proper cleaning and maintenance as directed in our instructions booklet.
8) The silicone material has a Shore durometer range which enables it to be soft to the touch. This simulates the feeling of real flesh.
9) Despite the notable softness of the silicone elastomer, it provides the proper elasticity and stretchiness to fit over syringes of the proper size, and maintain sufficient tension to grip the syringe and remain in place during use (it won't slip off).
10) The consistency of the material allows it further natural adherence to the syringe when heated and applied properly without air bubbles, further sealing the sleeve onto the syringe.

Figure 5:
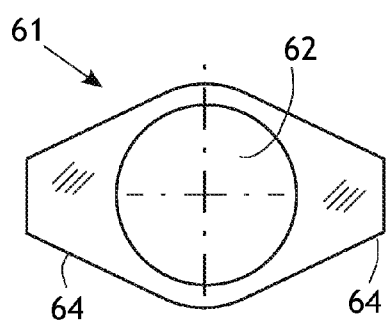
FIG. 5 is a plan view of the syringe sliding bail of the invention.

A further component of the invention is a sliding bail 61, shown in FIG. 5. The bail 61 is a flat object that includes a central opening 62 extending therethrough, the opening 62 having a diameter large enough to receive the barrel 22 of the syringe in freely sliding fashion, but smaller than the outside diameter of the sleeve 41. The bail 61 includes a pair of diametrically opposed tabs 64 that extend radially outwardly from the axis. As shown in FIGS. 1 and 6, the tabs 64 extend outwardly from the syringe beyond the tabs 34 at the proximal end of the syringe.

Figure 6:
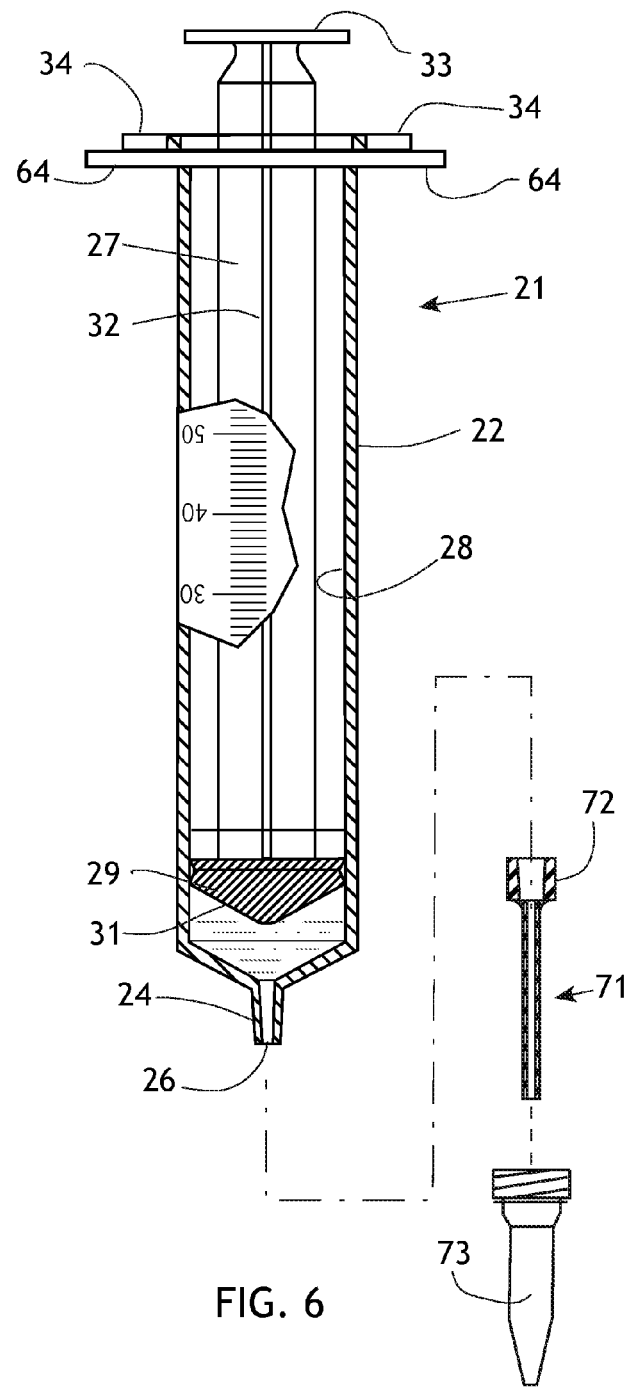
FIG. 6 is an exploded cross-sectional view showing the use of the syringe, cannula, and supply vial according to the invention.

With regard to FIG. 6, the invention may also provide a cannula 71 that comprises a thin tubular structure having a proximal end 72 adapted to be removably secured to the distal stem 24 of the syringe 21 by a frictional complementary fit, threaded engagement, or the like. The cannula 71 extends longitudinally a sufficient length to extend into a typical vial 73 that is commonly used to package, freeze, sell, and distribute human seminal fluid. The cannula 71 may be frictionally secured to the stem 24, then dipped into the vial 73, and the plunger 27 may be withdrawn to generate suction that draws the contents of the vial into the syringe for self-fertilization use. The cannula may also be used to draw seminal fluid from a specimen cup or other container.

The self-fertilization method of the invention includes an optional first step of securing the cannula 71 to the stem 24 of the syringe, and then seminal fluid is drawn into the syringe 21 (through the cannula 71, if used) by withdrawing the plunger 2. The cannula is removed and the stem 24 is capped to retain the fluid. The sliding bail 61 is then joined to the syringe barrel 22 and placed at the proximal end thereof. The sleeve 41 is then installed by inserting the distal end of the capped syringe into the open end 43 of the sleeve, and slidably worked into place. The elastic sleeve forms a seal with the barrel 22, and placing a finger on the discharge opening 51 traps air within the sleeve, and enables the user to push the sleeve proximally onto the barrel 22. This process is reiterated until the capped tip extends through the passageway 53 in the head of the sleeve. Prior to using the inseminator the cap is removed and the loaded inseminator is introduced into the vagina.

It may be appreciated that the inseminator approximates the size and feel of a typical penis, and may be used by a woman in the traditional way to aid in having an orgasm. At the appropriate moment, ideally when the distal tip 51 is proximate the cervical os, the plunger 27 may be depressed to discharge the seminal fluid. It is believed that discharging the seminal fluid in the midst of or just following an orgasm increases the potential for fertilization to be successful. After the device is used, the sliding bail 61 may be employed by pushing the tabs 64 and slidably working it along the barrel 42 in the distal direction to peel the proximal end of the sleeve 41 from the barrel of the syringe. The sleeve may be removed and cleaned in boiling water or compatible antiseptic techniques, and the syringe may be disposed and replaced for subsequent use.

The foregoing description of the preferred embodiments of the invention has been presented for purposes of illustration and description. It is not intended to be exhaustive or to limit the invention to the precise form disclosed, and many modifications and variations are possible in light of the above teaching without deviating from the spirit and the scope of the invention. The embodiment described is selected to best explain the principles of the invention and its practical application to thereby enable others skilled in the art to best utilize the invention in various embodiments and with various modifications as suited to the particular purpose contemplated. It is intended that the scope of the invention be defined by the claims appended hereto.

The invention claimed is:

1. Apparatus for performing insemination in a human being, including:
   a sleeve comprising a generally tubular body having an open proximal end and a closed distal end;
   said sleeve including a head formed at the closed distal end;
   said sleeve being fabricated of a soft, supple, high tensile strength elastomer and including a discharge opening extending axially through said head;
   a syringe having a rigid tubular barrel, said barrel having an outside diameter and length dimensioned to be assembled to and received within said tubular body of said sleeve in an elastic, non-slip manner, said assembly having approximately the size and configuration of a human penis;
   said barrel having a narrow distal opening extending axially therethrough and disposed proximate to said discharge opening of said sleeve;
   said syringe including a plunger received within said tubular barrel and translatable reciprocally therein from a proximal direction to take in fluid through said narrow distal opening, to a distal direction to eject the fluid from said narrow distal opening and out of said discharge opening of said sleeve.

2. The apparatus of claim 1, wherein said head has an oblate bulbous configuration with a radius of curvature greater than the radius of said tubular body.

3. The apparatus of claim 2, further including a plurality of channels formed in the outer surface of said head and extending longitudinally parallel to the axis of the assembly to permit fluid flow past said outer surface of said head.

4. The apparatus of claim 3, further including a shallow recess formed in said outer surface and disposed to extend about said discharge opening of said head.

5. The apparatus of claim 4, wherein said plurality of channels extend to and radiate from said shallow recess in said head.

6. The apparatus of claim 1, further including a sliding bail comprised of a flat body having a central opening with a diameter large enough to receive said barrel of said syringe in slidable fashion, but smaller than the outside diameter of said tubular body of said sleeve; and, a pair of tab handles extending in diametrical opposition to said central opening.

7. The apparatus of claim 1, wherein said barrel includes a tapered distal portion connected to a narrow stem projecting axially, and said narrow distal opening extends concentrically through said stem.

8. The apparatus of claim 7, wherein said discharge opening includes an axially extending passageway in said head that receives said stem of said barrel in elastic, sealing engagement.

9. The apparatus of claim 7, further including a cannula having one end configured to be releasably engaged with said stem, and having a length sufficient to access fluid within a deep narrow vial.

10. Apparatus for performing insemination in a human being, including:

a syringe having a rigid barrel, a plunger, and a distal opening, said syringe being adapted to take up and store seminal fluid;

a sleeve comprising a generally tubular body having an open proximal end and a closed distal end and an oblate head at the closed distal end;

said sleeve being fabricated of a soft, supple, high tensile strength elastomer and configured as a dildo to mimic the size, look, and feel of a human penis;

a discharge opening extending axially through said head of said sleeve;

said sleeve being assembled to said barrel of said syringe to provide rigidity to said sleeve;

said assembly being usable as a dildo to penetrate and stimulate the vagina; and, said plunger being operable to eject the seminal fluid into the vagina adjacent to the cervical opening.

\* \* \* \* \*